United States Patent
Nayar

(10) Patent No.: US 9,855,319 B2
(45) Date of Patent: Jan. 2, 2018

(54) STABILIZATION OF FACTOR VIII WITHOUT CALCIUM AS AN EXCIPIENT

(71) Applicant: Advantech Bioscience Farmacêutica LTDA, Barueri (BR)

(72) Inventor: Rajiv Nayar, Danville, CA (US)

(73) Assignee: ADVANTECH BIOSCIENCE FARMACÊUTICA LTDA, San Paulo (BR)

( * ) Notice: Subject to any disclaimer, the term of this patent is extended or adjusted under 35 U.S.C. 154(b) by 0 days.

(21) Appl. No.: 15/120,274

(22) PCT Filed: Mar. 30, 2015

(86) PCT No.: PCT/BR2015/000045
§ 371 (c)(1),
(2) Date: Nov. 30, 2016

(87) PCT Pub. No.: WO2015/149144
PCT Pub. Date: Oct. 8, 2015

(65) Prior Publication Data
US 2017/0080059 A1    Mar. 23, 2017

Related U.S. Application Data

(60) Provisional application No. 61/973,280, filed on Apr. 1, 2014.

(51) Int. Cl.
| | | |
|---|---|---|
| A61K 38/37 | (2006.01) | |
| A61K 9/19 | (2006.01) | |
| A61K 47/18 | (2017.01) | |
| A61K 47/02 | (2006.01) | |
| A61K 47/26 | (2006.01) | |

(52) U.S. Cl.
CPC ............... *A61K 38/37* (2013.01); *A61K 9/19* (2013.01); *A61K 47/02* (2013.01); *A61K 47/183* (2013.01); *A61K 47/26* (2013.01)

(58) Field of Classification Search
CPC .......... A61K 38/37; A61K 9/19; A61K 47/02; A61K 47/183; A61K 47/26
See application file for complete search history.

(56) References Cited

U.S. PATENT DOCUMENTS

| 5,733,873 | A | 3/1998 | Osterberg et al. |
|---|---|---|---|
| 5,763,401 | A | 6/1998 | Nayar |
| 5,874,408 | A | 2/1999 | Nayar |
| 6,171,825 | B1 | 1/2001 | Chan et al. |
| 6,599,724 | B1 | 7/2003 | Mikaelsson et al. |
| 6,780,614 | B2 | 8/2004 | Negrier et al. |
| 6,887,852 | B1 | 5/2005 | Paik et al. |
| 2003/0099618 | A1 | 5/2003 | Couto et al. |
| 2004/0229335 | A1 | 11/2004 | Zhang et al. |
| 2009/0035807 | A1 | 2/2009 | McCellan et al. |
| 2009/0263866 | A1 | 10/2009 | Wilson et al. |
| 2011/0039302 | A1 | 2/2011 | Kaufman et al. |
| 2011/0198286 | A1 | 8/2011 | Niazi |
| 2013/0184216 | A1 | 7/2013 | Besman et al. |
| 2014/0051832 | A1 | 2/2014 | Demasi et al. |
| 2017/0009269 | A1 | 1/2017 | Ozturk |
| 2017/0065683 | A1 | 3/2017 | Nayar |
| 2017/0067013 | A1 | 3/2017 | Ozturk et al. |

FOREIGN PATENT DOCUMENTS

| CZ | 290342 B6 | 7/2002 |
|---|---|---|
| WO | 2011/012725 A1 | 2/2011 |
| WO | 2011/062926 A2 | 5/2011 |

OTHER PUBLICATIONS

Izutsu, Therapeutic proteins, methods and protocols, Humana press, edited by C. Mark Smales and David C. James, 2005, pp. 287-292.*
International Preliminary Report on Patentability corresponding to International Patent Application No. PCT/BR2015/000045, completed Mar. 17, 2016.
International Search Report with Written Opinion corresponding to International Patent Application No. PCT/BR2015/000045, dated Oct. 6, 2015.
Dierickx (1986) "In vitro interaction of organic copper (II) compounds with soluble glutathione S-transferases from rat liver," Res. Commun. Chem. Pathol. Pharmacol. 51:285-288.
Kompala et al. (2005) "Optimization of High Cell Density Perfusion Bioreactors," In; Cell Culture Technology for Pharmaceutical and Cell-Based Therapies. Eds.: Ozturk et al. CRC Press. pp. 387-416.
Ohashi et al. (2001) "Perfusion Cell Culture in Disposable Bioreactors," In; The Proceedings of the 17th ESACT Meeting Tylösand, Sweden, Jun. 10-14, 2001. pp. 403-409.
Woodside et al. (1998) "Mammalian Cell Retention Devices for Stirred Perfusion Bioreactors," Cytotechnology. 28 (1-3):163-175.
International Preliminary Report on Patentability corresponding to International Patent Application No. PCT/BR2015/000019, completed Mar. 9, 2016.
International Preliminary Report on Patentability corresponding to International Patent Application No. PCT/BR2015/000025, completed Apr. 19, 2016.

(Continued)

*Primary Examiner* — Julie Ha
*Assistant Examiner* — Li Ni Komatsu
(74) *Attorney, Agent, or Firm* — Lathrop Gage LLP; James H. Velema, Esq.

(57) ABSTRACT

The present invention provides a novel albumin-free formulation of recombinant Factor VIII that does not require calcium ions as an added formulation excipient. The absence of calcium chloride in the formulation results in a number of improvements and benefits for a Factor VIII formulation. This invention allows a Factor VIII formulation that can be lyophilized more efficiently as the absence of calcium ions will increase primary glass transition of the amorphous phase. The absence of free calcium ions in the formulation will also improve the stability of the formulation as metal-dependent oxidation reactions will be avoided and the protein molecule will not be subjected to chemical instabilities. Finally, the absence of calcium will further simplify the Factor VIII formulation by reducing the number of excipients in the formulation.

15 Claims, 12 Drawing Sheets

(56) References Cited

OTHER PUBLICATIONS

International Preliminary Report on Patentability corresponding to International Patent Application No. PCT/BR2015/000044, completed Apr. 16, 2016.
International Search Report with Written Opinion corresponding to International Patent Application No. PCT/BR2015/000019, dated Oct. 7, 2015.
International Search Report with Written Opinion corresponding to International Patent Application No. PCT/BR2015/000025, dated Oct. 7, 2015.
International Search Report with Written Opinion corresponding to International Patent Application No. PCT/BR2015/000044, dated Oct. 7, 2015.

* cited by examiner

STABILIZATION OF FACTOR VIII WITHOUT CALCIUM AS AN EXCIPIENT

CROSS-REFERENCE TO RELATED APPLICATIONS

This application is a 35 U.S.C. §371 filing of international application number PCT/BR2015/000045, filed Mar. 30, 2015, which is based on and claims priority of U.S. provisional application No. 61/973,280 filed Apr. 1, 2014. The entire contents of which are incorporated herein by reference.

FIELD

This application relates generally to pharmaceutical formulations and particularly to a lyophilized formulation for rFVIII which is stabilized without albumin (albumin-free) and without any addition of divalent cations, such as calcium chloride, to the final formulation.

BACKGROUND

There are a number of albumin-free rFVIII formulations on the market using stabilization and formulation matrix excipients, such as, sodium chloride, glycine, mannitol, sucrose, trehalose, histidine, and calcium chloride. Calcium chloride is considered an essential component in the formulation because Factor VIII is a large hetero-dimer molecule where the heavy and light chains are held together by a metal ion bridge of divalent cations such as calcium and copper ions. All the current formulations contain calcium chloride, which has been assumed to be essential in order to maintain Factor VIII integrity and stability. The concentration of calcium chloride in the various formulations varies from 1.7 mM to 5 mM. It has been shown recently the calcium ($Ca^{2+}$) is necessary for the generation of Factor VIII cofactor activity but that $Ca^{2+}$ did not affect heavy chain-light chain binding affinity. It has been shown that Factor VIII contains two $Ca^{2+}$ binding sites with different affinities and that the cofactor activity of Factor VIII can be reconstituted from heavy chain and light chain only when both chains are preactivated by $Ca^{2+}$.

DETAILED DESCRIPTION

Objectives

The objective that led to this invention was to determine if rFactor VIII could be formulated into a stable lyophilized formulation without any calcium chloride in the formulation matrix. There are numerous references in the literature and prior art that imply the importance of adding divalent cations, in particular, calcium chloride, as a necessary excipient in the formulation matrix. We wanted to test this hypothesis or assumption and evaluate the structural integrity and stability of rFVIII in formulations with and without calcium chloride. The rFVIII was characterized by a number of analytical tools that measure with high sensitivity the molecular hydrodynamic radius of the protein and tertiary conformation of the protein. The hydrodynamic radius was measured using dynamic light scattering techniques to evaluate any changes in the molecular size of the protein. Any changes in the tertiary conformation of the protein in the presence or absence of added calcium chloride was analyzed by second-derivative UV spectroscopy that detects changes around the micro-environment of the Factor VIII molecule around its aromatic amino acids. To our surprise, no significant differences could be seen in rFVIII formulations with or without calcium chloride. Furthermore, to our surprise, the stability profiles under 2-8° C. and under accelerated temperature conditions of 40° C. showed that both formulations with and without calcium chloride were similar.

Having a rFVIII formulations without calcium chloride as an excipient provides several useful advantages. First, a simple formulation with one less formulation excipient to analyze and not restrict the choice of excipients that would have the potential of precipitating or forming strong complexes with calcium ions. Second, a calcium-free formulation would have a higher primary glass transition temperature and make lyophilization simpler and faster as the product could be lyophilized at higher shelf temperature during primary drying. Third, the absence of free calcium ions in the formulation is also beneficial for avoiding metal ion assisted oxidation of proteins that would affect the stability of the molecule through chemical instability mechanisms.

Specific Embodiments

Example 1

Example 1 shows that there was no difference in the recoveries of factor VIII activity across lyophilization between formulations with and without $CaCl_2$.

TABLE 1

Factor VIII bioactivity (IU/ml) by COATEST: Recovery across freeze-drying.

| COATEST | Frz, pre-lyo | Lyo, T = 0 | FD recovery | Formulation (mg/ml) (NaCl/CaCl$_2$/Sucrose/pH) |
|---|---|---|---|---|
| F8-E | 1211 | 962 | 79% | 18/ - - - /3suc/6.5 |
| F8-F | 1148 | 891 | 78% | 18/0.25Ca/3suc/6.5 |
| F8-G | 1289 | 971 | 75% | 18/ - - - /3suc/7.0 |
| F8-H | 1229 | 999 | 81% | 18/0.25Ca/3suc/7.0 |

F8-E and F8-G have no CaCl$_2$ as a formulation excipient.

Example 2

Figure 1A:
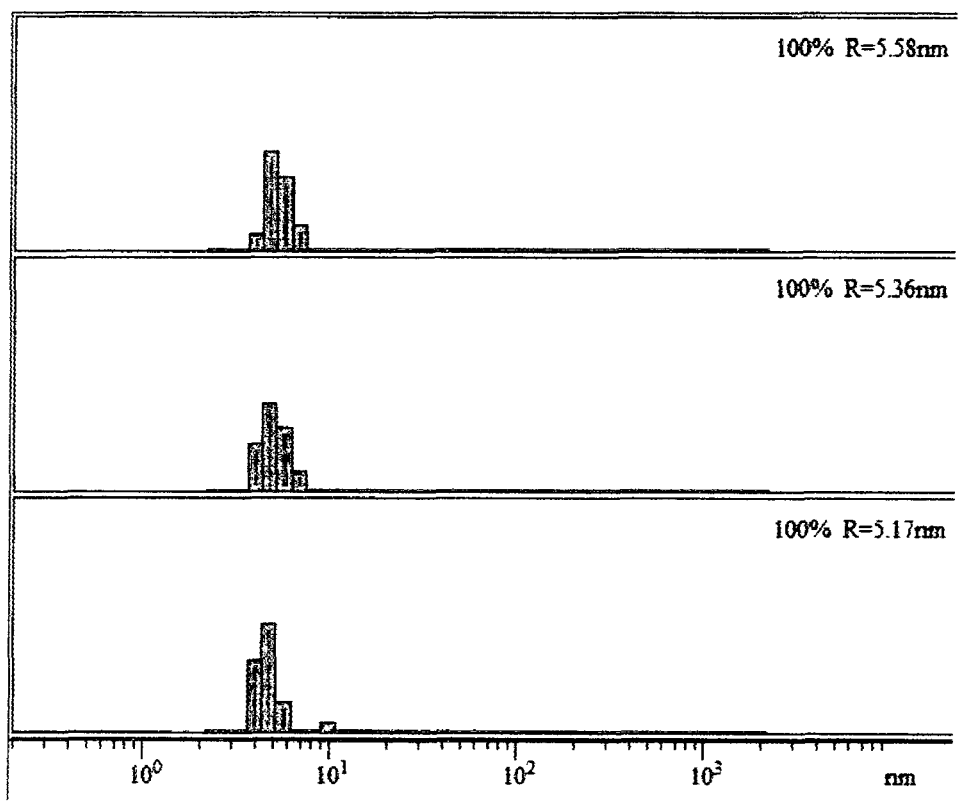
FIGS. 1A and 1B are histograms from Dynamic Light Scattering of F8-E (A) and F8-F (B) formulations where the formulation of F8-E comprises 308 mM NaCl/10 mM histidine, pH 6.5/9 mM sucrose/100 ppm polysorbate 80 and no added $CaCl_2$. The formulation of F8-F comprises 308 mM NaCl/10 mM histidine, pH 6.5/9 mM sucrose/100 ppm polysorbate 80 and 1.7 mM $CaCl_2$. The histograms show the molecular weight (MW) normalized distribution and the hydrodynamic radius of the protein.
Figure 1B:
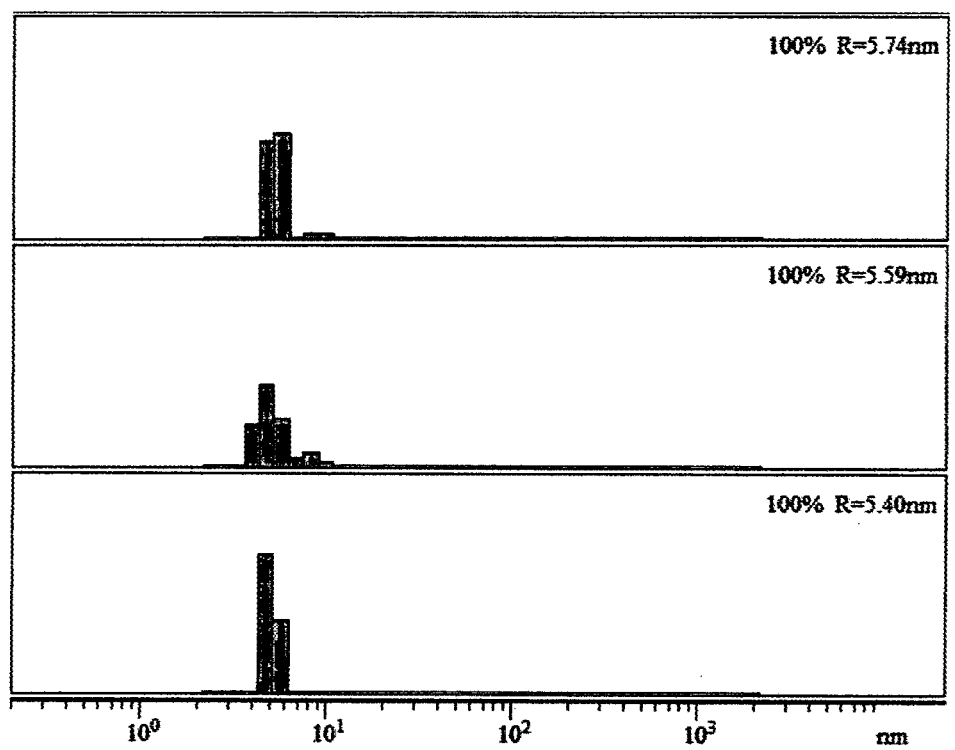
Figure 2A:
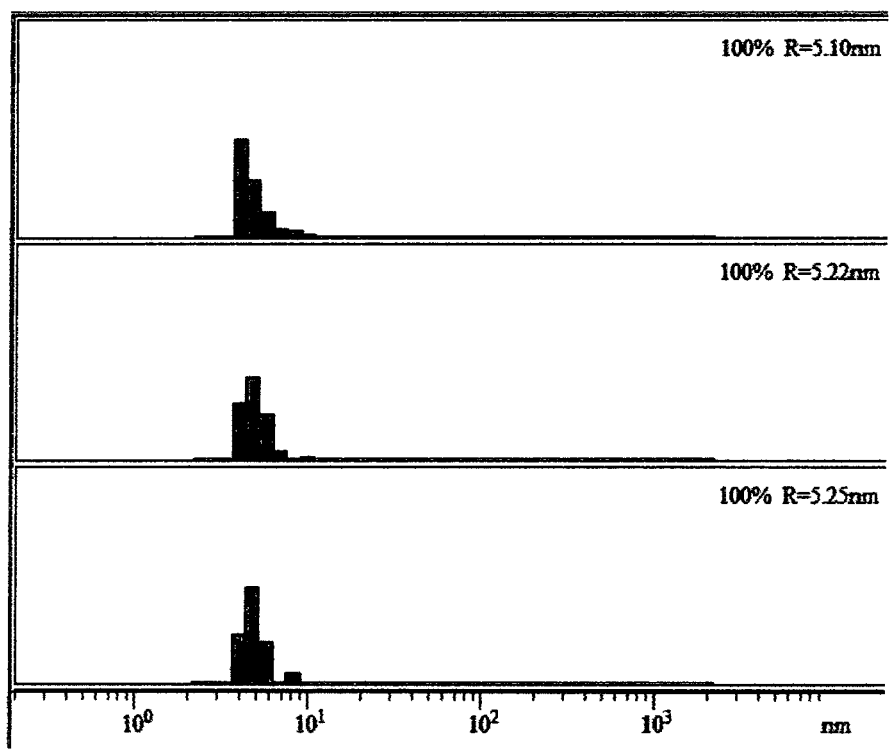
FIGS. 2A and 2B are histograms from Dynamic Light Scattering of F8-G (A) and F8-H (B) formulations where the formulation of F8-E comprises 308 mM NaCl/10 mM histidine, pH 7.0/9 mM sucrose/100 ppm polysorbate 80 and no added $CaCl_2$. The formulation of F8-F comprises 308 mM NaCl/10 mM histidine, pH 7.0/9 mM sucrose/100 ppm polysorbate 80 and 1.7 mM $CaCl_2$. The histograms show the molecular weight (MW) normalized distribution and the hydrodynamic radius of the protein.
Figure 2B:
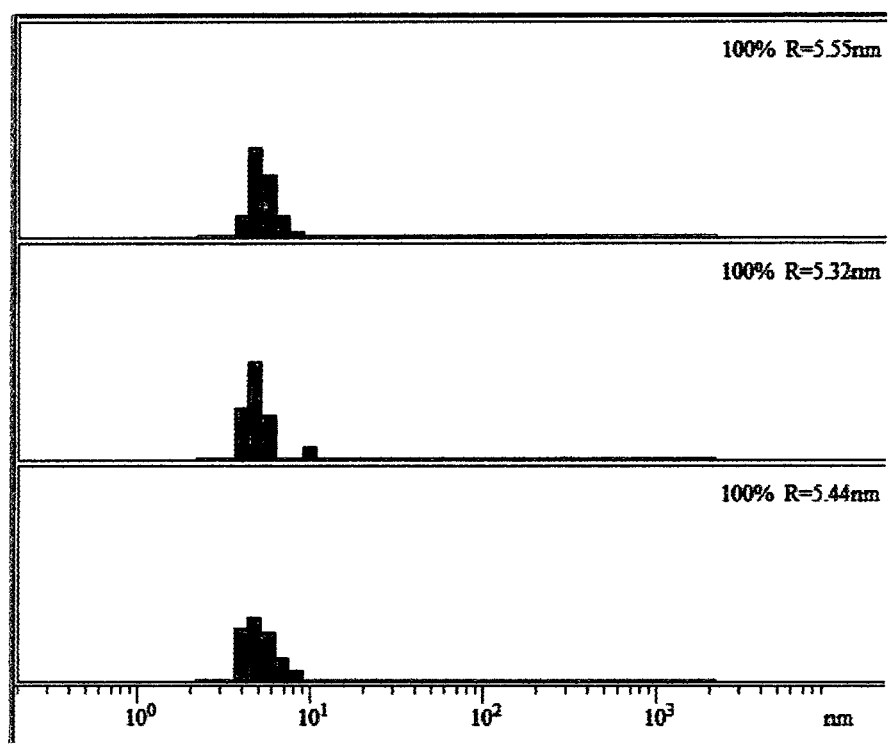
Figure 3A:
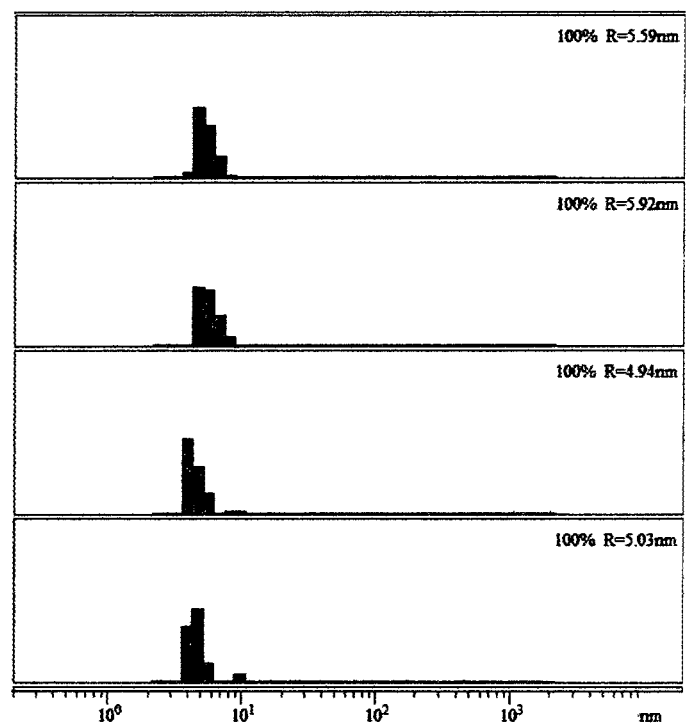
FIGS. 3A and 3B are histograms from Dynamic Light Scattering of F8-I and F8-J (A) and F8-K and F8-L (B) formulations where the formulation of F8-I and F8-J comprises 308 mM NaCl/10 mM histidine, 9 mM trehalose/100 ppm polysorbate 80 and no added $CaCl_2$ at pH 6.5 and 7.0, respectively. The formulations of F8-K and F8-L comprises of 308 mM NaCl/10 mM histidine, pH 7.0/9 mM trehalose/100 ppm polysorbate 80 and 1.7 mM $CaCl_2$ at pH 6.5 and 7.0, respectively. The histograms show the MW normalized distribution and the hydrodynamic radius of the protein.
Figure 3B:
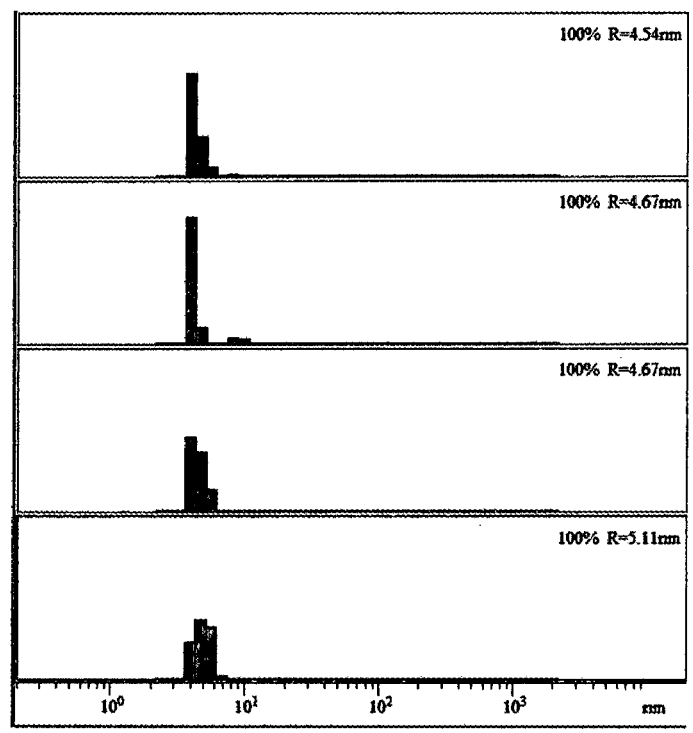

Example 2 shows that there was no difference in the hydrodynamic radius of factor VIII between formulations with and without $CaCl_2$. Table 2 summarizes the results from formulations made with sucrose and Table 3 summarizes the results from formulations made with trehalose. The representative histograms are shown in FIGS. 1-3

TABLE 2

Hydrodynamic radius for F8-E, -F, -G, and -H formulations.

|  | F8-E | F8-F | F8-G | F8-H |
|---|---|---|---|---|
|  | 5.58 | 5.74 | 5.10 | 5.55 |
|  | 5.36 | 5.59 | 5.22 | 5.32 |
|  | 5.17 | 5.40 | 5.25 | 5.44 |
| Average | 5.37 | 5.58 | 5.19 | 5.44 |
| S.D. | 0.21 | 0.17 | 0.08 | 0.12 |
| pH | 6.5 | 6.5 | 7.0 | 7.0 |
| CaCl | − | + | − | + |

TABLE 3

Hydrodynamic radius for F8-I, -J, -K, and -L formulations.

|  | F8-I | F8-J | F8-K | F8-L |
|---|---|---|---|---|
|  | 5.59 | 4.94 | 4.54 | 4.67 |
|  | 5.92 | 5.03 | 4.67 | 5.11 |
| Average | 5.76 | 4.99 | 4.61 | 4.89 |
| S.D. | 0.23 | 0.06 | 0.09 | 0.31 |
| pH | 6.5 | 6.5 | 7.0 | 7.0 |
| CaCl | − | + | − | + |

Example 3

Figure 4:
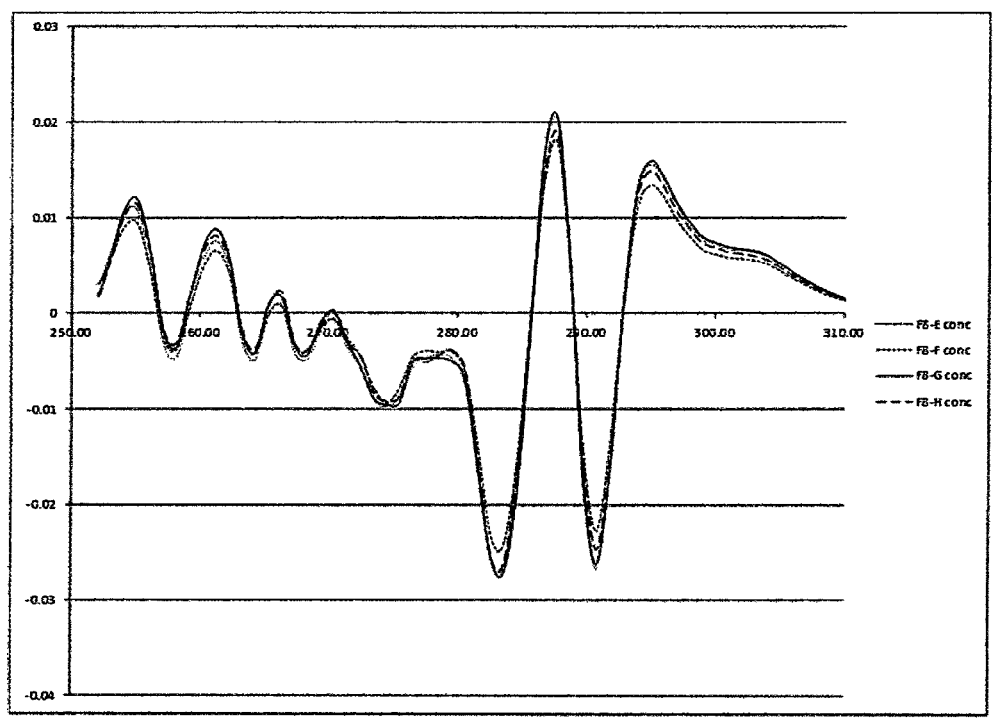
FIG. 4 shows the profiles of the tertiary structural conformations of rFVIII in formulations with and without $CaCl_2$. F8-E (dotted line) and F8-G (solid line) are formulated without calcium chloride and F8-F (dashed line) and H (large dashed line) are formulated with calcium chloride. Formulations are described in FIGS. 1 and 2, above. The x-axis is the wavelength and y-axis is the second-derivative values of the absorbance.
Figure 5:
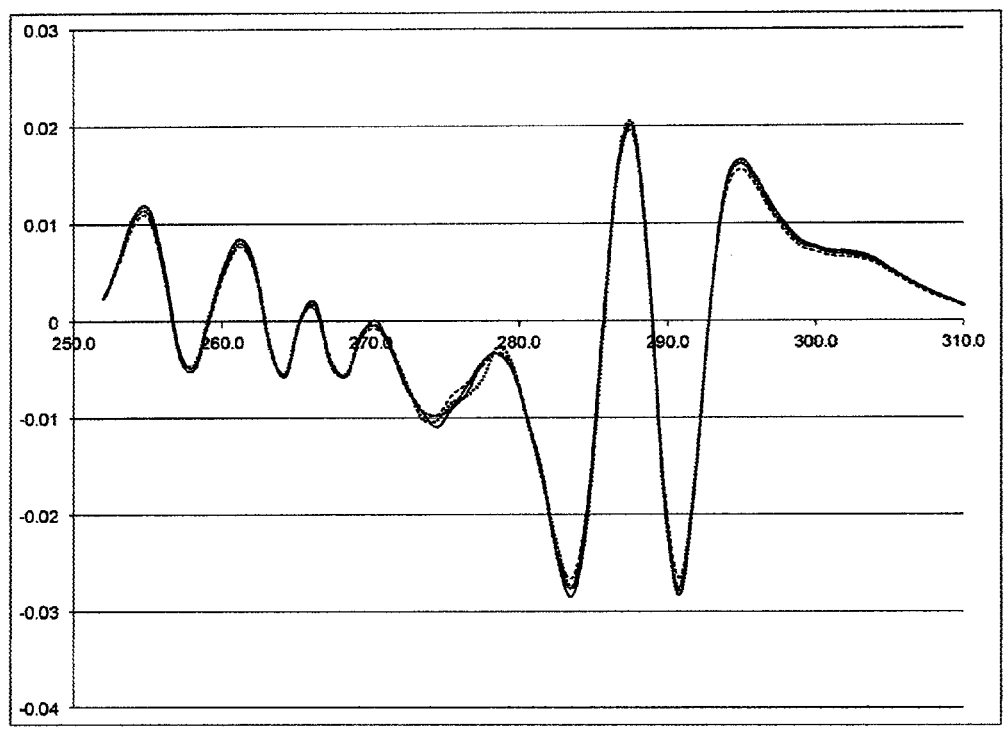
FIG. 5 shows the profiles of the tertiary structural conformations of rFVIII in formulations with and without $CaCl_2$. F8-I (solid line) and F8-K (dashed line) are formulated without calcium chloride and F8-J (dotted line) and L (large dashed line) are formulated with calcium chloride. Formulations are described in FIG. 3, above. The x-axis is the wavelength and y-axis is the second-derivative values of the absorbance.

Example 3 shows that there are no significant differences in the tertiary conformation of rFVIII in formulations with and without calcium chloride. The tertiary conformation of rFVIII was evaluated by second-derivative spectroscopy and changes in the microenvironments around three aromatic amino acids, phenylalanine, tyrosine, and tryptophan were quantified by their peak positions and relative peak to trough distances expressed as ratios. The 2 dUV profiles of rFVIII formulations with and without calcium chloride formulated in sucrose and formulated in trehalose FIGS. 4 and 5, respectively. The 2 dUV parameters are summarized in Tables 4 and 5.

TABLE 4

2d UV parameters for F8-E, -F, -G, and -H formulations.

|  | F8-E | F8-F | F8-G | F8-H |
|---|---|---|---|---|
| Peak Ratios | F8-220-9 | F8-220-11 | F8-220-13 | F8-220-15 |
| A'/B | 1.14 | 1.19 | 1.15 | 1.17 |
| A'/C | 3.89 | 4.10 | 3.89 | 4.06 |
| B/C | 3.43 | 3.45 | 3.37 | 3.48 |
| Peak Positions | | | | |
| Phe nm | 257.84 | 257.84 | 257.87 | 257.84 |
| Tyr-Trp nm | 283.28 | 283.24 | 283.34 | 283.21 |
| Trp nm | 290.78 | 290.78 | 290.78 | 290.81 |
| pH | 6.5 | 6.5 | 7.0 | 7.0 |
| CaCl$_2$ | — | 9 mM | — | 9 mM |

TABLE 5

2d UV parameters for F8-I, -J, -K, and -L formulations.

| | F8-I conc | F8-J conc | F8-K conc | F8-L conc |
|---|---|---|---|---|
| Peak Ratios | | | | |
| A'/B | 1.08 | 1.09 | 1.09 | 1.10 |
| A'/C | 3.68 | 3.70 | 3.64 | 3.63 |
| B/C | 3.40 | 3.40 | 3.34 | 3.30 |
| Peak Positions | | | | |
| Phe nm | 257.84 | 257.84 | 257.81 | 257.84 |
| Tyr-Trp nm | 283.50 | 283.56 | 283.47 | 283.47 |
| Trp nm | 290.81 | 290.81 | 290.81 | 290.81 |
| pH | 6.5 | 6.5 | 7.0 | 7.0 |
| CaCl$_2$ | — | 9 mM | — | 9 mM |

Example 4

Example 4 shows the stability profiles of the rFVIII formulated with and without calcium chloride as an added excipient. Formulations were lyophilized and evaluated under accelerated storage temperatures of 40° C.

Figure 6:
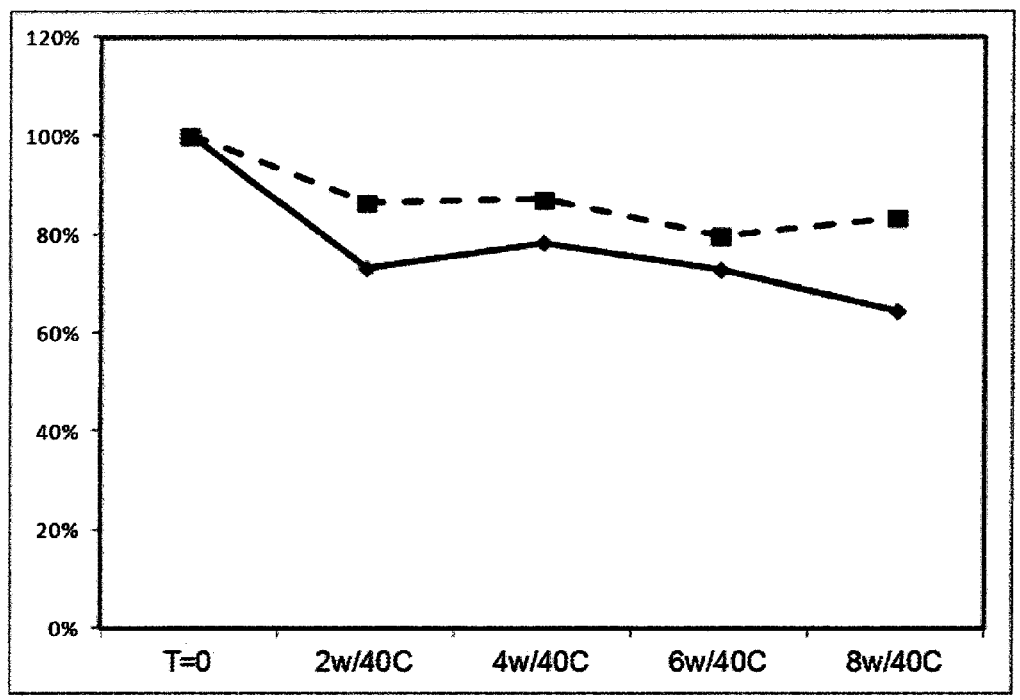
FIG. 6 shows similar stability profiles of rFVIII formulations with and without $CaCl_2$ as a formulation excipient under accelerated storage temperature of 40° C. over 8 weeks of storage. The formulation containing calcium (dashed line) was formulated in 18 mg/ml NaCl, 0.25 mg/ml calcium chloride, 3 mg/ml sucrose and 20 mM histidine at pH 6.5. The formulation without calcium (solid line) was formulated in 18 mg/ml NaCl, 3 mg/ml sucrose and 20 mM histidine at pH 6.5. The x-axis is the storage time/temperature in weeks and y-axis is percent initial potency (at t=0).
Figure 7:
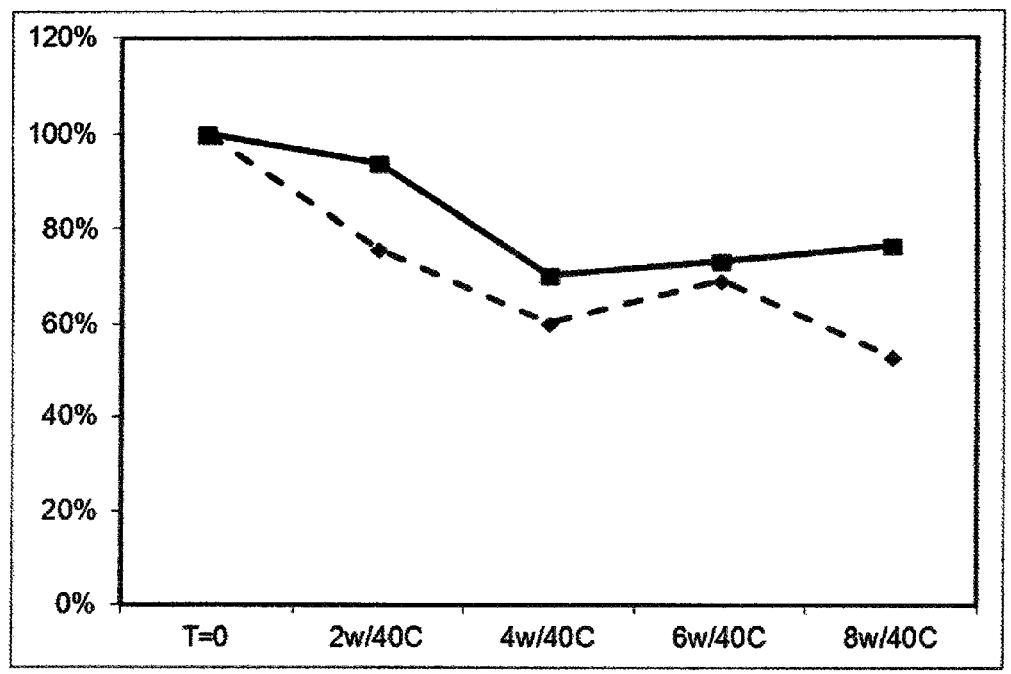
FIG. 7 shows similar stability profiles of rFVIII formulations with and without $CaCl_2$ as a formulation excipient under accelerated storage temperature of 40° C. The formulation containing calcium (solid line) was formulated in 18 mg/ml NaCl, 0.25 mg/ml calcium chloride, 3 mg/ml sucrose and 20 mM histidine at pH 7.0. The formulation without calcium (dashed line) was formulated in 18 mg/ml NaCl, 3 mg/ml sucrose and 20 mM histidine at pH 7.0. The x-axis is the storage time/temperature in weeks and y-axis is percent initial potency (at t=0).
Figure 8:
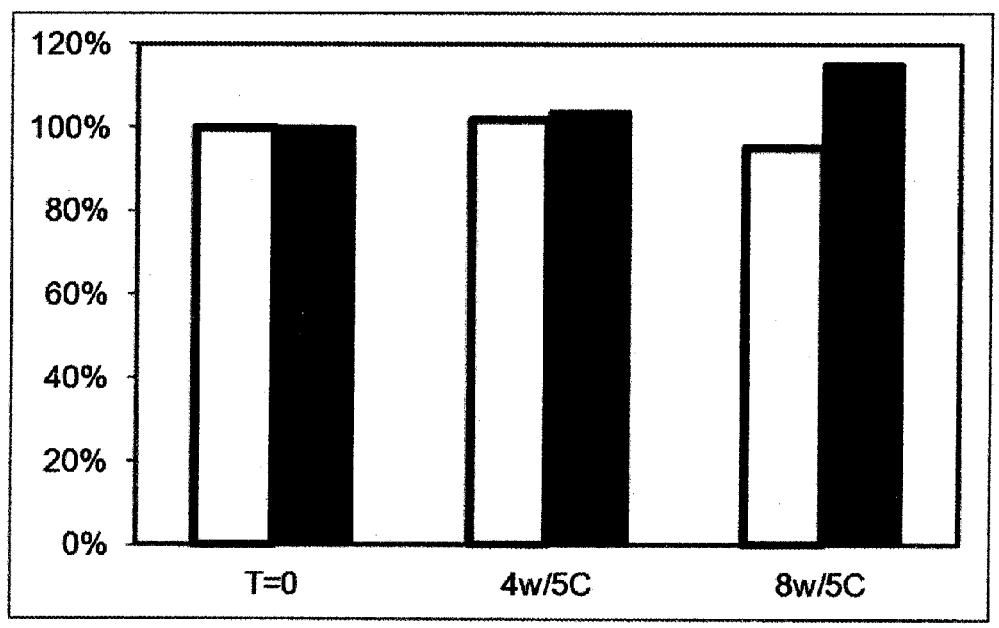
FIG. 8 shows stability of $Ca^{2+}$ free rFVIII formulations during storage at 2-8° C. with no loss of FVIII potency. Empty bar is the Formulation at pH 6.5 and Filled bar is the Formulation at pH 7.0. The x-axis is the storage time/temperature in weeks and y-axis is percent initial potency (at t=0).
Figure 9:
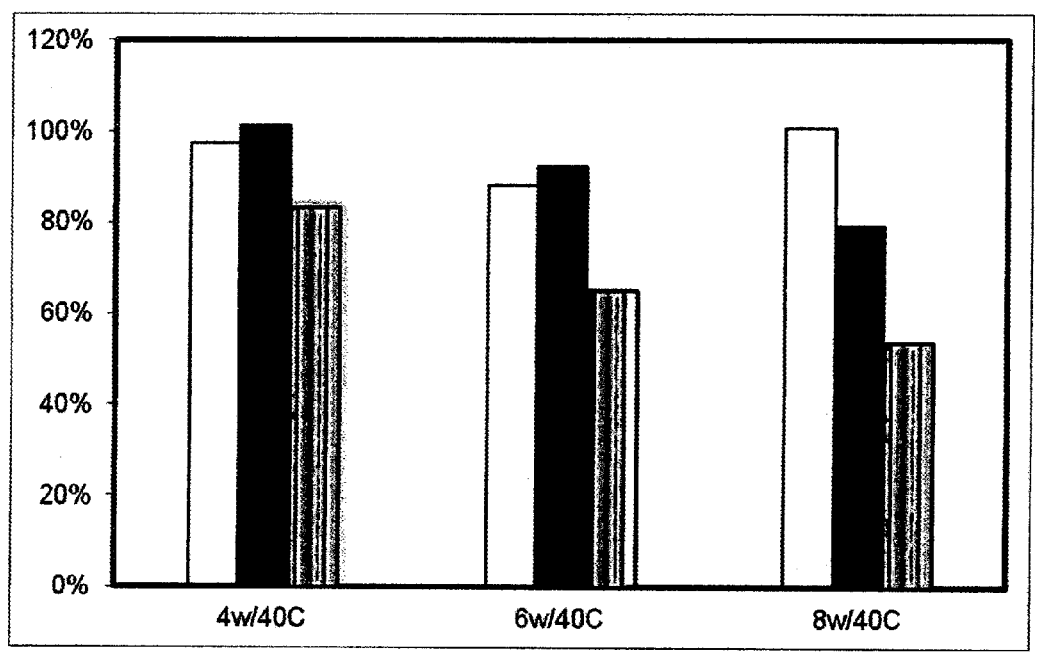
FIG. 9 shows the comparative stability of $Ca^{2+}$ free rFVIII formulations with a commercial Factor VIII formulations containing $CaCl_2$ in its formulation during storage at an accelerated temperature of 40° C. Empty bar is the $Ca^{2+}$ free FVIII formulation at pH 6.5. Filled bar is the $Ca^{2+}$ free FVIII formulation at pH 7.0. The gradient bar is the commercial Factor VIII formulation containing $CaCl_2$ in its formulation. The x-axis is the storage time/temperature in weeks and y-axis is percent initial potency (at t=0).

FIGS. 6 and 7 show stability profiles of rFVIII in sucrose formulations at pH 6.5 and 7.0, respectively. Both formulations with and without calcium chloride show similar losses of FVIII activity over the storage time. FIG. 8 shows that there was no significant loss of Factor VIII activity in calcium-free formulations storage at 2-8° C. over an 8 week period. FIG. 9 shows the relative stabilities of rFVIII formulations with and without calcium chloride. The formulation with calcium chloride is a commercial Factor VIII formulation.

The above examples are intended to illustrate the invention and it is thought variations will occur to those skilled in the art. Accordingly, it is intended that the scope of the invention should be limited only by the claims below.

SUMMARY

The albumin-free and calcium-free formulation of Factor VIII is a lyophilized formulation that is a pharmaceutically acceptable drug product, which is suitable for treating hemophilia and, therefore, may be used to prepare a medicament to treat such disease. The lyophilized product is stable with respect to its molecular integrity, hydrodynamic radius, cofactor activity, and tertiary conformation. The formulation can be rapidly reconstituted (within 30 seconds) for convenience and patient administration. The formulation comprises of a mixture of salts, amino acids, and sugars, such as sucrose, trehalose, but unlike the prior art, does not have calcium chloride as a formulation excipient. The absence of calcium chloride results in a formulation with a higher primary glass transition of the amorphous phase, thus making the lyophilization process more efficient. The absence of free calcium ions in the formulation is also beneficial as it does not restrict the choice of excipients that would have the potential of precipitating or forming strong complexes with calcium ions. Examples of such excipients are amino acids such as histidine, arginine, and lysine that are conceivable buffers and stabilizers in Factor VIII formulations. The absence of calcium ions also is beneficial for avoiding metal ion assisted oxidation of proteins that would affect the stability of the molecule through chemical instability mechanisms.

Preferred formulations are stable, albumin-free and calcium free lyophilized rFVIII preparations, which when reconstituted in water contain up to about 310 mM NaCl, up to about 50 mM Histidine providing a pH of about 6.5 to 7.5, up to about 20 mM of sucrose or trehalose, and about 50-2000 IU recombinant Factor VIII per milliliter, but devoid of divalent cations such as Calcium 2+ ion as a formulation excipient. A particularly preferred stable albumin-free and calcium-free lyophilized rFVIII formulation is devoid of divalent cations, such as Ca $Ca^{2+}$, as a formulation excipient, but contains 308 mM NaCl, 20 mM histidine, capable of providing a pH of about 6.5 to 7.5, about 9 mM sucrose or trehalose and about 50 to 2000 IU recombinant FVIII per milliliter. B Domain deleted Factor VIII having a specific activity of between 8000 and 15000 IU per milligram is the preferred form of recombinant Factor VIII.

The invention claimed is:

1. A stable, albumin-free and calcium-free lyophilized recombinant Factor VIII (rFVIII) preparation comprising NaCl, histidine, sucrose or trehalose, and rFVIII, wherein the preparation comprises, when reconstituted in water,
   up to 310 mM NaCl;
   up to 50 mM histidine, pH 6.5-7.5;
   up to 20 mM sucrose or trehalose;
   50-2,000 IU rFVIII/ml;
   with no divalent cations as a formulation excipient.

2. The preparation of claim 1, wherein the rFVIII is B-domain deleted protein that has a specific activity between 8,000 and 15,000 IU/mg.

3. The preparation of claim 1, wherein the omitted divalent cation is $Ca^{++}$.

4. A stable albumin-free and calcium-free lyophilized rFVIII preparation comprising, when reconstituted in water,
   308 mM NaCl;
   20 mM histidine, pH 6.5-7.0;
   9 mM sucrose or 9 mM trehalose;
   50-2000 IU rFVIII/ml;
   with no divalent cations as a formulation excipient.

5. The preparation of claim 4, wherein the rFVIII is B-domain deleted protein that has a specific activity between 8,000 and 15,000 IU/mg.

6. The preparation of claim 4, wherein the omitted divalent cation is $Ca^{++}$.

7. A stable, albumin-free and calcium-free lyophilized rFVIII preparation comprising, when reconstituted in water,
   up to 310 mM NaCl;
   up to 50 mM histidine, pH 6.5-7.5;
   up to 20 mM sucrose or trehalose; and
   50-2,000 IU B-domain deleted rFVIII/ml.

8. A method of treating hemophilia in a subject in need thereof, the method comprising administering the preparation of claim 1 to the subject, thereby treating hemophilia in the subject.

9. A method of treating hemophilia in a subject in need thereof, the method comprising administering the preparation of claim 4 to the subject, thereby treating hemophilia in the subject.

10. A method of treating hemophilia in a subject in need thereof, the method comprising administering the preparation of claim 2 to the subject, thereby treating hemophilia in the subject.

11. A method of treating hemophilia in a subject in need thereof, the method comprising administering the preparation of claim 5 to the subject, thereby treating hemophilia in the subject.

12. A method of preparing the preparation of claim 1, the method comprising mixing NaCl, histidine, sucrose or trehalose, and rFVIII in the absence of divalent cations.

13. A method of preparing the preparation of claim 4, the method comprising mixing NaCl, histidine, sucrose or trehalose, and rFVIII in the absence of divalent cations.

14. A method of preparing the preparation of claim 2, the method comprising mixing NaCl, histidine, sucrose or trehalose, and rFVIII in the absence of divalent cations.

15. A method of preparing the preparation of claim 5, the method comprising mixing NaCl, histidine, sucrose or trehalose, and rFVIII in the absence of divalent cations.

\* \* \* \* \*